(12) United States Patent
Brown et al.

(10) Patent No.: US 9,029,163 B2
(45) Date of Patent: May 12, 2015

(54) METHOD FOR GENERATION OF AUTOMATED DENATURATION GRAPHS

(75) Inventors: Richard Brown, East Falmouth, MA (US); Burleigh Hutchins, West Brookfield, MA (US); Ernesto Freire, Baltimore, MD (US)

(73) Assignee: Avia Biosystems, Inc., East Falmouth, MA (US)

( * ) Notice: Subject to any disclaimer, the term of this patent is extended or adjusted under 35 U.S.C. 154(b) by 873 days.

(21) Appl. No.: 13/214,357

(22) Filed: Aug. 22, 2011

(65) Prior Publication Data

US 2012/0045841 A1    Feb. 23, 2012

Related U.S. Application Data

(60) Provisional application No. 61/375,920, filed on Aug. 23, 2010.

(51) Int. Cl.
- *G01N 1/38* (2006.01)
- *G01N 33/68* (2006.01)
- *G01N 21/64* (2006.01)
- *G01N 35/10* (2006.01)

(52) U.S. Cl.
CPC .............. *G01N 33/6803* (2013.01); *G01N 1/38* (2013.01); *G01N 35/1065* (2013.01); *G01N 35/1072* (2013.01)

(58) Field of Classification Search
None
See application file for complete search history.

(56) References Cited

U.S. PATENT DOCUMENTS

| | | |
|---|---|---|
| 5,306,510 A | 4/1994 | Meltzer |
| 5,935,859 A | 8/1999 | Elliott et al. |
| 6,063,339 A | 5/2000 | Tisone et al. |
| 6,203,759 B1 | 3/2001 | Pelc et al. |
| 6,232,085 B1 | 5/2001 | Pantoliano et al. |
| 6,488,829 B1 | 12/2002 | Schroeder et al. |
| 6,551,557 B1 | 4/2003 | Rose et al. |
| 6,589,791 B1 | 7/2003 | LaBudde et al. |
| 6,592,825 B2 | 7/2003 | Pelc et al. |
| 6,764,648 B1 | 7/2004 | Roach et al. |
| 7,244,396 B2 | 7/2007 | Chait et al. |
| 7,790,462 B2 | 9/2010 | Fournier et al. |
| 7,858,041 B2 | 12/2010 | Muraishi et al. |
| 8,609,040 B2 | 12/2013 | Brown et al. |
| 2001/0014477 A1 | 8/2001 | Pelc et al. |
| 2001/0016177 A1 | 8/2001 | Pelc et al. |
| 2001/0020588 A1 | 9/2001 | Adourian et al. |
| 2001/0048899 A1 | 12/2001 | Marouiss et al. |
| 2002/0176803 A1 | 11/2002 | Hamel et al. |
| 2003/0062265 A1 | 4/2003 | King et al. |

(Continued)

OTHER PUBLICATIONS

Pradeep, L. et al. "Differential Salt-induced Stabilization of Structure in the Initial Folding Intermediate Ensemble of Barstar," J. Mol. Biol. (2002) 324, 331-347.*

(Continued)

*Primary Examiner* — Yelena G Gakh
*Assistant Examiner* — Michelle Adams
(74) *Attorney, Agent, or Firm* — Nields, Lemack & Frame, LLC

(57) ABSTRACT

A system and method for creating a plurality of denaturation curves is disclosed. In accordance with certain embodiments, one variable, such as salt content, pH or another parameter, is varied to create a plurality of different buffer solutions. Each is then used to create a denaturation graph. The plurality of denaturation graphs allows analysis of the effect of that variable on protein stability.

16 Claims, 8 Drawing Sheets

(56) References Cited

U.S. PATENT DOCUMENTS

| | | | |
|---|---|---|---|
| 2003/0219906 A1* | 11/2003 | Giaquinta et al. | 436/180 |
| 2004/0157266 A1 | 8/2004 | Oas et al. | |
| 2008/0226498 A1 | 9/2008 | Stylli et al. | |
| 2009/0298186 A1 | 12/2009 | Brigham-Burke et al. | |
| 2012/0045367 A1 | 2/2012 | Brown et al. | |

OTHER PUBLICATIONS

Caprette, D. R. "Working with Stock Solutions" on the Internet at URL <http://www.ruf.rice.edu/~bioslabs/methods/solutions/stocks.htm>; available at URL <https://web.archive.org/web/20131205075858/http://www.ruf.rice.edu/~bioslabs/methods/solutions/stocks.htm> on Dec. 17, 2006.*

Office Action mailed Oct. 3, 2012 in co-pending U.S. Appl. No. 13/214,361.

Journal of the Korean Chemical Society, 2005, vol. 49, No. 5, pp. 479-487, "Analysis of the m-value Change in the Equilibrium Unfolding of Hydrophobic Core Variant Ubiquitin", Park, et al.

International Search Report/Written Opinion mailed Apr. 9, 2012 in co-pending PCT application No. PCT/US2011/048799.

Notice of Allowance mailed Sep. 26, 2013 in U.S. Appl. No. 13/214,361.

Supplemental Notice of Allowance mailed Nov. 8, 2013 in U.S. Appl. No. 13/214,361.

Final Rejection mailed Apr. 3, 2013 in co-pending U.S. Appl. No. 13/214,361.

* cited by examiner

METHOD FOR GENERATION OF AUTOMATED DENATURATION GRAPHS

This application claims priority from U.S. Provisional Patent Application Ser. No. 61/375,920, filed Aug. 23, 2010, the disclosure of which are incorporated herein by reference in its entirety.

BACKGROUND OF THE INVENTION

Protein therapeutics is the fastest growing segment of the biotechnology and pharmaceutical industry. Protein therapeutics includes monoclonal antibodies, recombinant proteins, chimeric proteins and other protein receptor constructs. This segment is expected to reach over $70 billion in sales by 2011.

A major hurdle in the development and use of proteins as pharmaceutical drugs is the ability to store, transport and deliver them in a safe stable form. It is well known that factors, such as temperature, solvent, ligands, excipients, pH, and salt concentration, affect a particular protein's stability. The identification of buffer, ligand and excipient conditions that maximize the stability and eliminate protein aggregation is critical during development and often requires the evaluation of hundreds of conditions. This combination of buffer, ligand and excipients conditions is referred to as the storage formulation throughout this disclosure. Unfortunately, it is difficult to vary all of the various parameters to determine the ideal storage formulation for a particular protein.

There are different ways to measure protein stability and each involves disrupting the protein structure through either physical or chemical means. This disruption of the protein structure is referred to as denaturation.

Temperature is one of the most widely used physical denaturants. In this scenario, a protein is subjected to increasing temperature and the corresponding changes in its structure are recorded. One of the disadvantages of temperature denaturation is that proteins typically denature at temperatures at or above 60° C. However, in most instances, the temperatures of interest are physiological (about 37° C.), room (about 25° C.) and storage (4° C.). Thus, results from temperature-based denaturation tests must be extrapolated by more than 25° C. to understand the effects at the temperatures of interest. In addition, most proteins used as biologics undergo irreversible temperature denaturation, which precludes a meaningful calculation of thermodynamic stability at the temperatures of interest. In addition, a formulation that elicits a higher denaturation temperature does not necessarily result in a more stable protein at room temperature.

A second way to measure protein stability is through the use of chemical denaturants, such as urea or guanidine hydrochloride. This method permits measurements to be done at any desired temperature.

The structural stability of a protein is determined by its Gibbs energy of stability, $\Delta G$. This value, $\Delta G$, is a function of temperature, chemical denaturants and other physical and chemical variables. Using the common example of a two state model, where a protein is either folded (i.e. native) or unfolded (i.e. denatured), the protein can transition between these two states:

$N \Leftrightarrow U$, wherein N is the native (folded) state and U is the unfolded state.

Two different rate constants can be defined from this transitional equation. $K_f$ is the rate of the folding reaction; while $K_u$ is the rate of the unfolding reaction. Finally, the equilibrium constant, K, can be defined as the ratio of the unfolding rate to the folding rate, or $$K = \frac{K_u}{K_f}.$$

Furthermore, the Gibbs energy can be expressed in terms of K, as $$\Delta G = -RT \ln(K),$$

where R is the gas constant, T is the temperature, expressed in Kelvin and ln(K) is the natural log of K. Thus, if K is greater than one, the protein unfolds at a higher rate than it folds, and its Gibbs energy is negative. Conversely, if K is less than one, the protein unfolds at a slower rate than it folds, and its Gibbs energy is positive. Also, K is equal to the ratio of the concentration of protein in the unfolded state and the concentration of protein in the folded state K=[U]/[F].

In addition, it has been observed that, for chemical denaturants, a nearly linear relationship exists between the Gibbs energy and the concentration of the denaturant. This relationship may be expressed as $$\Delta G = \Delta G_0 - m^*[\text{denaturant}],$$

where $\Delta G_0$ is the intrinsic Gibbs energy, [denaturant] is the concentration of denaturant, and m is the multiplier, which is unique for a particular protein.

For a native/unfolded equilibrium, the fraction of protein molecules which are unfolded, or denatured, $F_d$, is given by:

$$F_d = \frac{K}{1+K},$$

where K is the equilibrium constant.

This equation can be used to allow calculation of a denaturation curve. When a protein changes from its folded state to an unfolded state, certain measurable characteristics of the protein also change. One such characteristic is the fluorescence of the protein.

While the preferred embodiment described in this application utilizes fluorescence emission (intrinsic or extrinsic) as a way to determine the degree of denaturation or unfolding of a protein, the disclosure is not limited to this technique. There are many physical observable properties and their associated instrumentation, in addition to fluorescence spectroscopy, that are sensitive to the degree of denaturation of a protein. These observable properties include, but are not limited to uv/vis spectroscopy, circular dichroism, nuclear magnetic resonance (NMR), infrared spectroscopy (IR) among others.

FIG. 1 shows a typical urea denaturation curve for an antibody. The y, or vertical, axis is a measure of the intrinsic fluorescence of the protein. The fluorescence of different dyes, usually known as protein probes, can also be used. The horizontal, or x, axis is the concentration of urea in solution with the protein. As can be seen, at a certain point, between 3M and 4M urea, the fluorescence of the protein changes dramatically, indicating that it has denatured.

The generation of the data needed to produce such a graph is laborious. In one scenario, a solution containing the protein and any excipients is prepared. A sample of this solution is then subjected to fluorescent light and the emission is recorded. This is the baseline fluorescence with no chemical denaturant. In some embodiments, an amount of urea is then added to the remainder of the solution, and the light test is repeated on a portion of this modified solution. An additional amount of urea is then added to the remainder of the solution and a third light test is performed. This process is repeated for the number of desired samples. The amount of urea added each time is a function of the desired granularity of the test, and the range of urea molarities to be included. Such a method is prone to errors, as there are cumulative errors due to the constant addition of urea to the remaining solution. In this stepwise urea addition method, the process will result in the dilution of the protein and also a smaller fluorescence signal. In addition, since the solubility of urea is about 10.5M and a final 8M urea concentration is needed, the starting protein solution volume needs to be extremely small. The protein will be significantly diluted as the experiment progresses.

In another embodiment, a plurality of solutions, each with the protein, any excipients, and the proper amount of urea, is individually prepared. Each of these prepared solutions is then light tested to determine its fluorescence. While this method removes the cumulative errors associated with the previous method, it is extremely time consuming, especially for a large number of samples.

The resulting graph, such as that shown in FIG. 1, shows the stability of a particular combination of buffer, ligand and excipient conditions in the presence of a chemical denaturant. More stable combinations have a similarly shaped graph, shifted to the right. Conversely, less stable combinations have a graph shifted to the left. The goal of this testing is to find a combination with the maximum stability in the presence of the chemical denaturant. This combination can then be used as the storage formulation for the protein as it is stored and shipped.

Given the increased importance of developing proteins for pharmaceutical purposes, there is a dearth of systems and methods available to aid in the determination of the ideal storage formulation in which the protein is most stable.

For example, denaturation graphs are an effective way to understand the stability of a protein in a particular buffer solution. However, as described above, the creation of denaturation graphs is tedious and error prone. Furthermore, the testing required to fully understand the effect of changing one or more components of that buffer solution is so labor intensive that it is rarely performed. A system and method for automatically creating a plurality of denaturation graphs would be beneficial.

SUMMARY OF THE INVENTION

A system and method for creating a plurality of denaturation curves is disclosed. In accordance with certain embodiments, one variable, such as salt content, excipients, ligands, pH or another chemical or physical parameters, are varied to create a plurality of different buffer solutions. Each is then used to create a denaturation graph. The plurality of denaturation graphs allows analysis of the effect of that variable on protein stability.

DETAILED DESCRIPTION OF THE INVENTION

Figure 1:
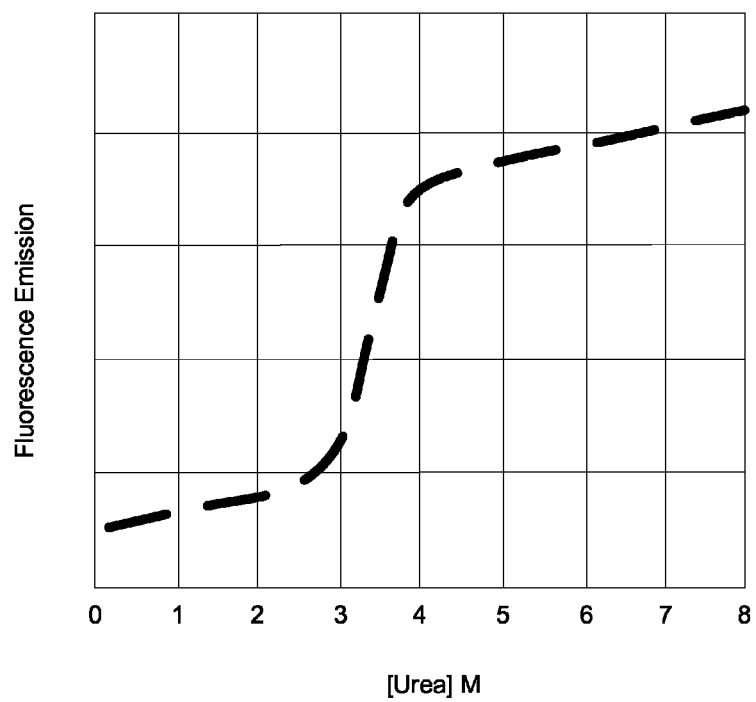
FIG. 1 is a denaturation graph of the prior art.

FIG. 1 shows a typical denaturation graph, used to determine the stability of a protein in the presence of a chemical denaturant, where the chemical denaturant can be urea, guanidinium hydrochloride (GuHCl) or other appropriate chemical. This graph shows the stability of the protein for a particular combination of buffer, ligand and excipients conditions. However, it is often useful to view a plurality of these graphs to understand how changes in the buffer, ligand or excipients affects the stability of the protein.

For example, for a particular combination, it may be of interest to understand how various concentrations of a compound, such as a salt, pH, ligand or other excipient, may affect the stability of the protein. For example, it may be of interest to measure the effects of different concentrations of salt in combination with a particular buffer and ligand. To do this, one may create four different formulations:

Formulation 1: solution with minimum salt and no denaturant

Formulation 2: solution with minimum salt and maximum denaturant

Formulation 3: solution with maximum salt and no denaturant

Formulation 4: solution with maximum salt and maximum denaturant

While the descriptions in this disclosure refer to certain formulations having no denaturant, it is understood that, in another embodiment, Formulations 1 and 3 contain a minimum amount of denaturant, which may be greater than 0, while Formulations 2 and 4 contain a maximum amount of denaturant.

To create a denaturation graph, one may begin by using only formulations 1 and 2. By combining these two formulations in different proportions, one can create a plurality of solutions, each with a minimum amount of salt and a varying amount of chemical denaturant. This plurality of solutions can be used to create a first denaturant graph.

Similarly, formulations 3 and 4 can be used to create a second denaturation graph, showing the stability of a solution with a maximum amount of salt with varying amounts of chemical denaturant.

A set of other graphs can also be created, each of which has a salt concentration between the minimum and maximum values. The particular number of graphs within the set is not particularly limited, and can be predetermined or arbitrary. For example, a denaturation graph showing the effect of chemical denaturant, with a salt concentration that is the average of the minimum and maximum values, may be created. In this scenario, a new formulation is created by mixing Formulation 1 and Formulation 3 in equal amounts. This new formulation has a salt concentration exactly halfway between the minimum and maximum values, with no chemical denaturant. Similarly, a second new formulation is created by mixing equal amounts of Formulation 2 and Formulation 4. This new formulation has a salt concentration exactly halfway between the minimum and maximum values, with a maximum amount of chemical denaturant. The denaturant graph for this salt concentration is then created as described above.

Figure 2:
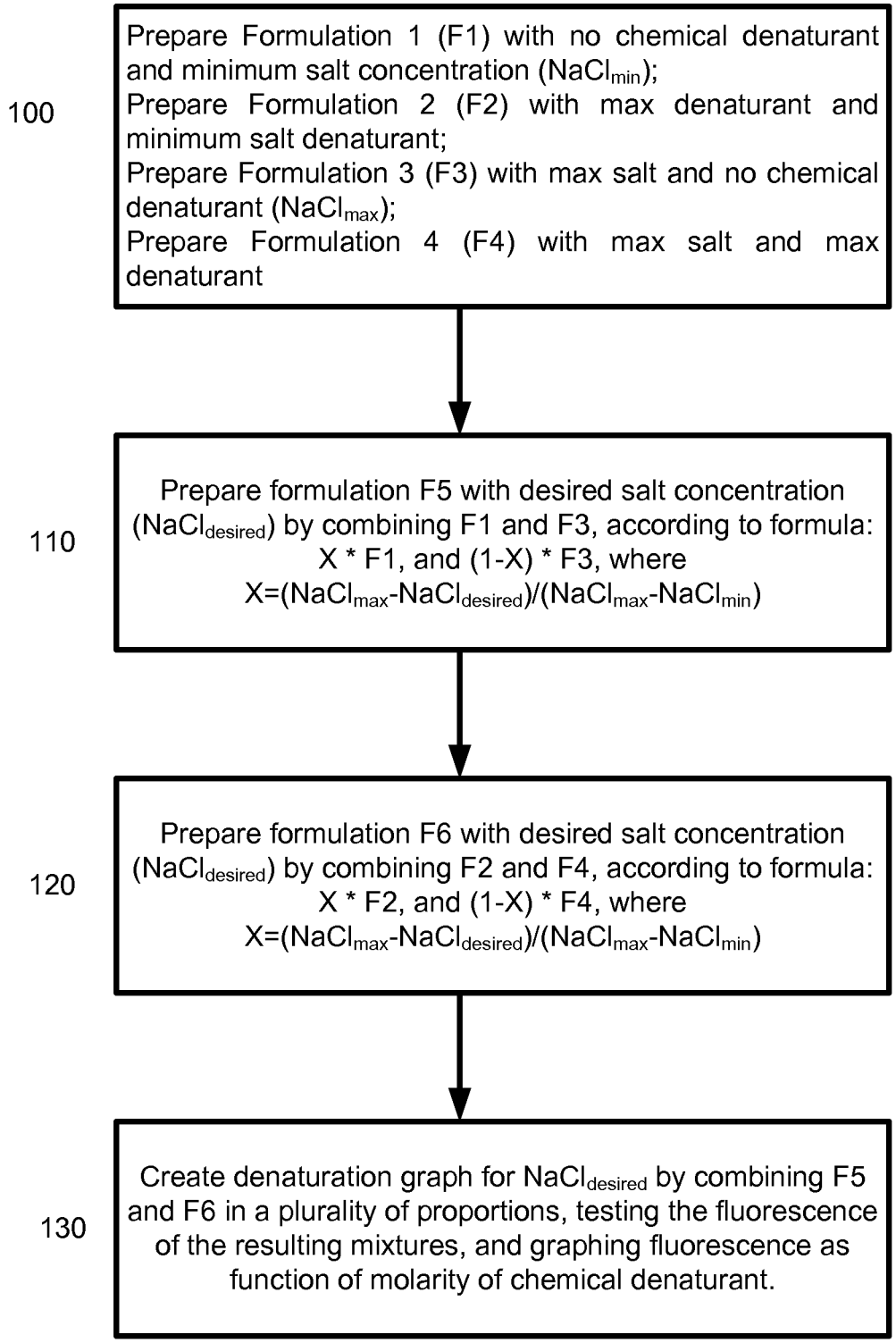
FIG. 2 is a flowchart illustrating a process to generate a denaturation graph with a desired salt concentration.

This process can be repeated a plurality of times to create the required or desired granularity of salt concentration. FIG. 2 shows a flowchart showing this sequence. In step 100, the four formulations, labeled F1 through F4, are prepared. These four formulations represent the four corners of the testing. In step 110, a fifth formulation, which has the desired amount of salt and no chemical denaturant is prepared, using the equation shown. This equation assumes a linear relationship and is used to create any desired concentration between the minimum salt concentration and the maximum salt concentration. Similarly, in step 120, a sixth formulation, which has the desired amount of salt and the maximum amount of chemical denaturant is prepared, using the equation shown. It should be noted that the fifth and sixth concentrations may each be prepared in a separate well or vessel, so as to be available for future use. However, in other embodiments, the fifth and sixth formulations need not be independently created. Rather, the formulations F1, F2, F3 and F4 may be combined in the specific ratios described by these equations in a single well or vessel, without the intermediate formulations F5, F6 being prepared in a separate vessel. Thus, the terms "fifth formulation" and "sixth formulation" are used to express the ratios of F1 and F3, and F2 and F4, respectively, even in the scenario where such formulations may not exist in an isolated vessel. Finally, as shown in step 130, using the fifth and sixth formulations, a denaturation graph can be prepared. For an eleven point graph, the F5 and F6 formulations may be combined as shown in Table 1 below.

TABLE 1

| Point Number | % of F5 | % of F6 |
|---|---|---|
| 1 | 100 | 0 |
| 2 | 90 | 10 |
| 3 | 80 | 20 |
| 4 | 70 | 30 |
| 5 | 60 | 40 |
| 6 | 50 | 50 |
| 7 | 40 | 60 |
| 8 | 30 | 70 |
| 9 | 20 | 80 |
| 10 | 10 | 90 |
| 11 | 0 | 100 |

Each of these points is prepared and then subjected to testing, where the observable property is measured. In one embodiment, this testing includes the measurement of the fluorescence emission of the protein itelf (intrinsic) or a fluorescence probe that is sensitive to protein denaturation after being excited with a light of a wavelength that is absorbed by the protein or fluorescence probe. The fluorescence of each data point is measured and recorded. The fluorescence is then plotted as a function of the molarity of the chemical denaturant. The result of this process is a denaturation graph. The process shown in FIG. 2 can be repeated for an arbitrary number of salt concentrations.

Figure 3:
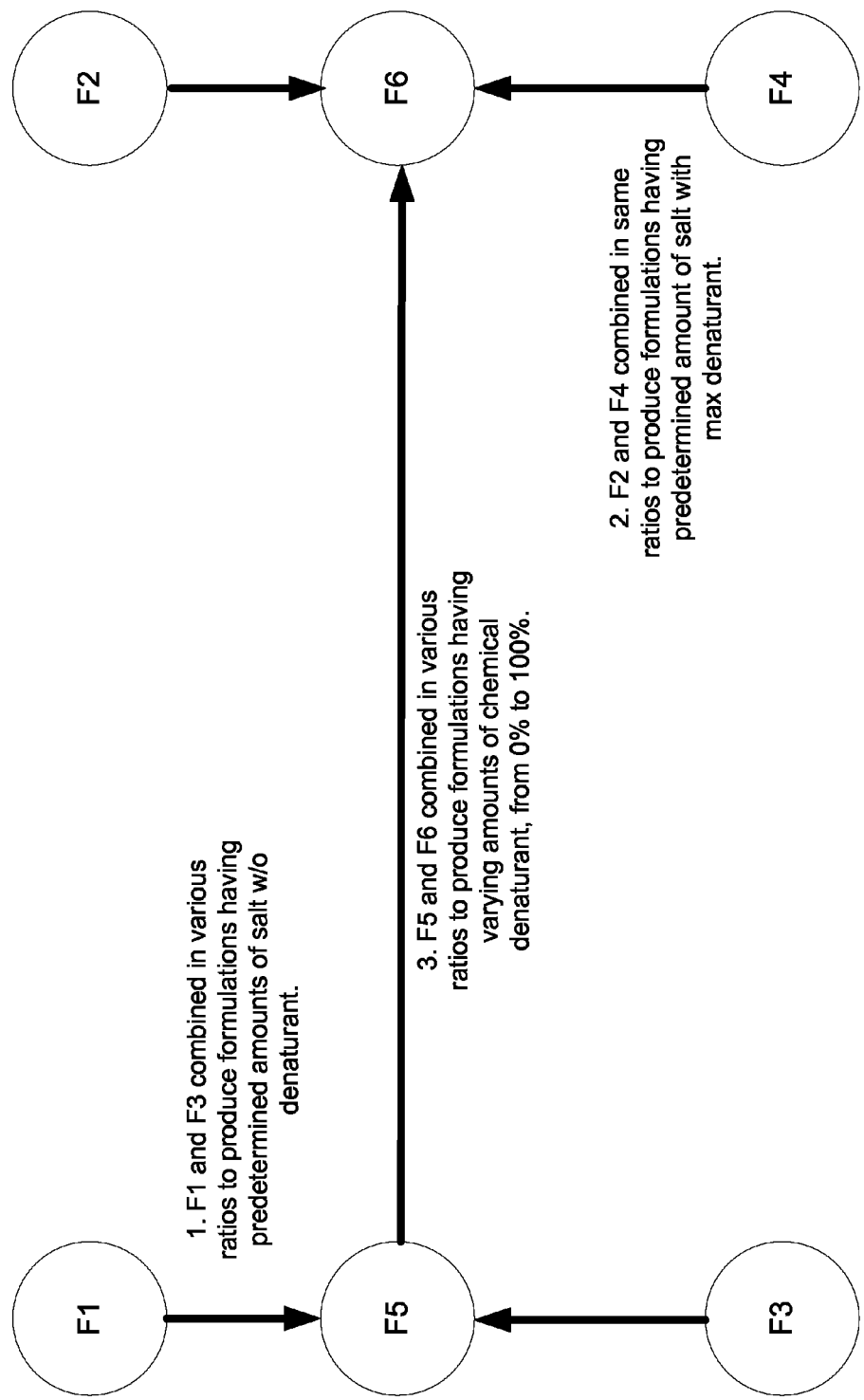
FIG. 3 is a graphical representation of the method of FIG. 2.

FIG. 3 graphically shows how the four concentrations are used to create the plurality of denaturation graphs. Step 1 shows that the two formulations without chemical denaturant F1, F3 are mixed in a predetermined proportion to create a fifth formulation F5. This formulation has a predetermined amount of salt, which is between the salt content in F1 and the salt content in F3. Typically, a linear model is used to determine the value of the salt in F5. For example, assume F1 has 0% salt and F3 has 5% salt. A formulation F5, having 2% salt, is made by combining F1 and F3 in a ratio of 3:2. However, other, non-linear models may be used to determine the content or amount of the variable parameter in the fifth formulation.

Step 2 shows that the two formulations with chemical denaturant F2, F4 are mixed in the same predetermined proportion to create a sixth formulation F6, having the same salt content as F5, but with a chemical denaturant.

Step 3 shows that the fifth formulation may be combined with the sixth formulation in decreasing amounts to create a plurality of formulations having a gradient of chemical denaturants. The fluorescence of each of this plurality of formulations is then measured and a denaturation graph may be created.

Using this method, a plurality of denaturation graphs may be generated, where each represents the effect of an increasing amount of chemical denaturant on a buffer having a specific amount of a variable. The number of different denaturation graphs is not limited by the disclosure. For example, salt in concentrations between 0% and 5% can be tested using steps of varying size. For example, a coarse test may be performed by testing at only 6 different concentrations (0%, 1%, 2%, 3%, 4%, and 5%). In another embodiment, a fine test may be performed by testing the salt concentration at every 0.1% (0%, 0.1% ... 4.8%, 4.9%, 5.0%). Of course, other step sizes are also within the scope of the disclosure.

In a similar way, the number of points that are tested to make each denaturation graph may be determined by the operator, and may be any arbitrary value. In some embodiments, a 24 point denaturation test is performed. However, other numbers of points, either greater and lesser, may be used.

Figure 4:
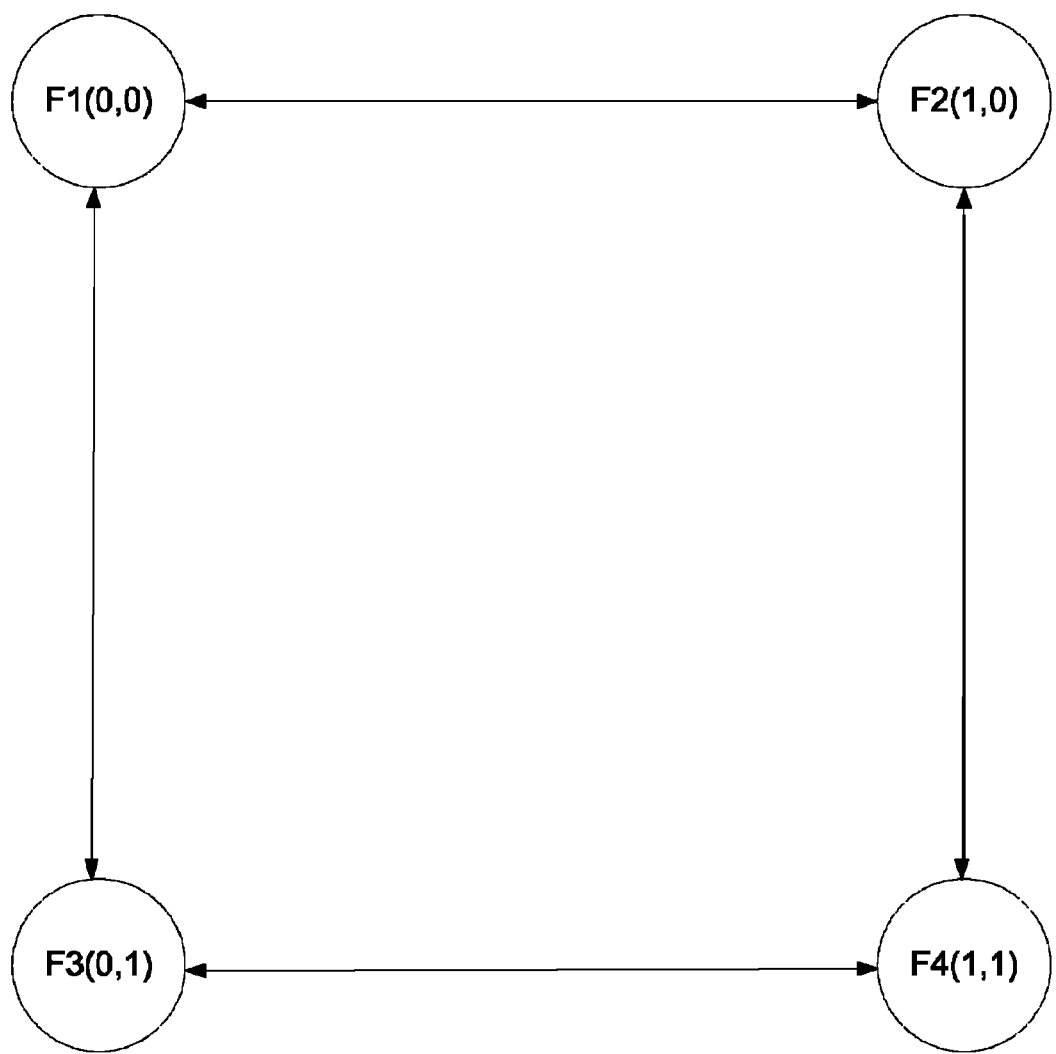
FIG. 4 is a graphical representation of the method to simultaneously test two parameters.

In other embodiments, more than one variable may be tested at one time. FIG. 4 shows a graphical representation where two independent variables may be tested simultaneously. F1 is the formulation having a minimum amount of both variables ($V_1$, $V_2$). As such, for simplicity, it is labeled (0,0), although the minimum value of one or both variables may not be 0. F2 is the formulation having a maximum amount of $V_1$, and a minimum amount of variable $V_2$. As such, it is labeled (1,0). F3 is the formulation having a minimum amount of $V_1$, and a maximum amount of variable $V_2$. As such, it is labeled (0,1). Finally, F4 is a formulation having a maximum amount of $V_1$ and a maximum amount of variable $V_2$. To create any desired concentration of V1 and V2, the technique shown in FIG. 5 can be followed.

First, the process begins with the four formulations (F1, F2, F3, F4) described above, as shown in step 200. A fifth formulation, F5, is made which has the desired amount of V1 and the minimum amount of V2, as shown in step 210. A sixth formulation, F6, is made which has the desired amount of V1 and the maximum amount of V2, as shown in step 220. A seventh formulation F7 is then made by combining F5 and F6 according to the equation shown in step 230.

In another embodiment, intermediate formulations F5 and F6 are not prepared. Rather F1, F2, F3 and F4 are combined as shown in the following equation:

$$X*Y*F1, (1-X)*Y*F2, X*(1-Y)*F3, (1-X)*(1-Y)*F4,$$

where $X=(V1_{max}-V1_{desired})/(V1_{max}-V1_{min})$ and $Y=(V2_{max}-V2_{desired})/(V2_{max}-V2_{min})$ As an example, to produce a formulation having 40% V1 and 70% V2, using the above equations, one would combine the four formulations in the following percentages: 18% F1, 12% F2, 42% F3 and 28% F4.

Figure 5:
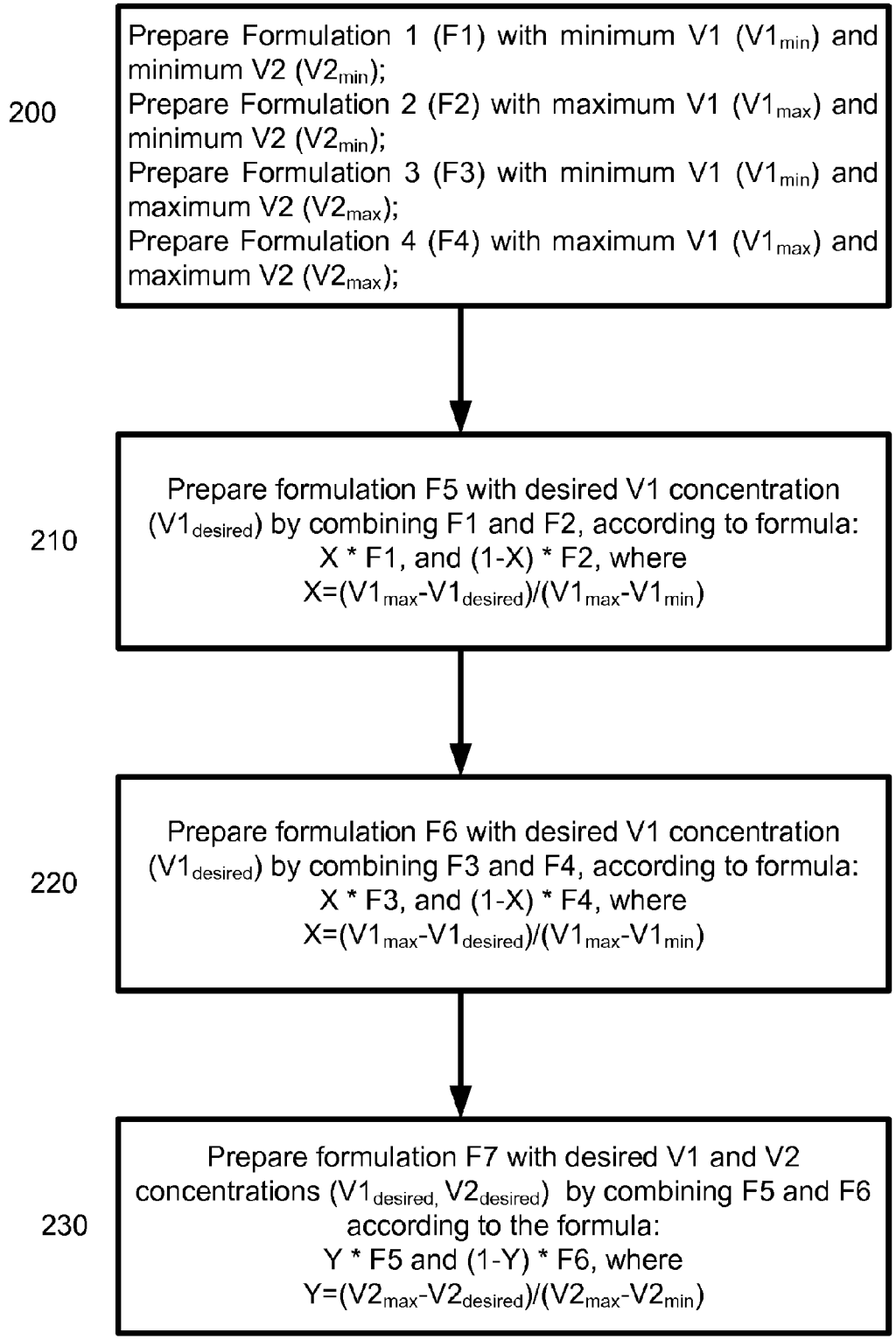
FIG. 5 is a flowchart illustrating a process to generate a formulation having two variables.

FIG. 5 shows the process to create the formulation having the desired amount of V1 and V2 with no denaturant. This process is then repeated for a second set of formulations, each corresponding to one of formulations F1-F4, except each having the maximum chemical denaturant. This process would yield a formulation F8 having the desired amount of V1 and V2 with maximum denaturant. These two formulations F7, F8 can then be combined in various proportions to generate a denaturation graph, as previously described.

Of course, the amounts of V1 and V2 can be independently modified to create a plurality of curves, each comprising a different composition of buffer solution.

While embodiments showing the generation of denaturation graphs having one and two variables is disclosed, the disclosure is not limited to these embodiments. Indeed, an arbitrary number of variables can be tested simultaneously by expanding the process shown in FIG. 5 to include the desired number of variables.

FIGS. 2 and 3 both disclose the use of four formulations to produce a plurality of denaturation curves. In other embodiments, three formulations may be used. In this embodiment, the first formulation is the formulation with no chemical denaturation and a minimum amount of the variable, similar to F1 in FIG. 3. The second formulation is a formulation with no chemical denaturant and a maximum amount of the variable, similar to F3. The third formulation is a formulation containing only the chemical denaturant. This third formulation is added in differing amount to the combination of F1 and F3 to create the denaturation graph. Other combinations of formulations may also be used to create the plurality of denaturation graphs. The important aspect is that these combinations can be automated so that a plurality of graphs may be relatively easily created in order to analysis the effect of a variable on protein stability.

Although the above description utilized formulations having varying salt concentrations, this is not the only parameter that can be tested. In addition to salt concentration, parameters include pH, ligands, chemical excipients, especially those approved by the FDA.

As mentioned above, to aid in the creation of these formulations and denaturation curves, automation may be employed. In this embodiment, shown in FIG. 6, an apparatus 300 having a controller 305 with a processing unit and a storage element is used. The storage element may be RAM, DRAM, ROM, Flash ROM, EEROM, magnetic media, or any other medium suitable to hold computer readable data and instructions. The instructions may be those necessary to execute the flowchart of FIG. 2 or FIG. 5. The processing unit may be a dedicated microcontroller, a personal computer or any other suitable computing device. In addition, the apparatus has a pump or siphon system 310, which allows it to extract liquid from a variety of wells, such as first well (F1), a second well (F2), a third well (F3) and a fourth well (F4) as shown in FIG. 3, in exact quantities and mix these liquids together, preferably in another well. The apparatus 300 also has a means to measure and record the fluorescence of the formulations, such as by using a commercially available fluorescence detector 330. The apparatus also includes one or more actuators 320 which can move the cannulas 340 from one position to another, so as to draw fluid from a first well (such as F1 in FIG. 3) and expel the fluid into a second well (such as F5 in FIG. 5).

Figure 6:
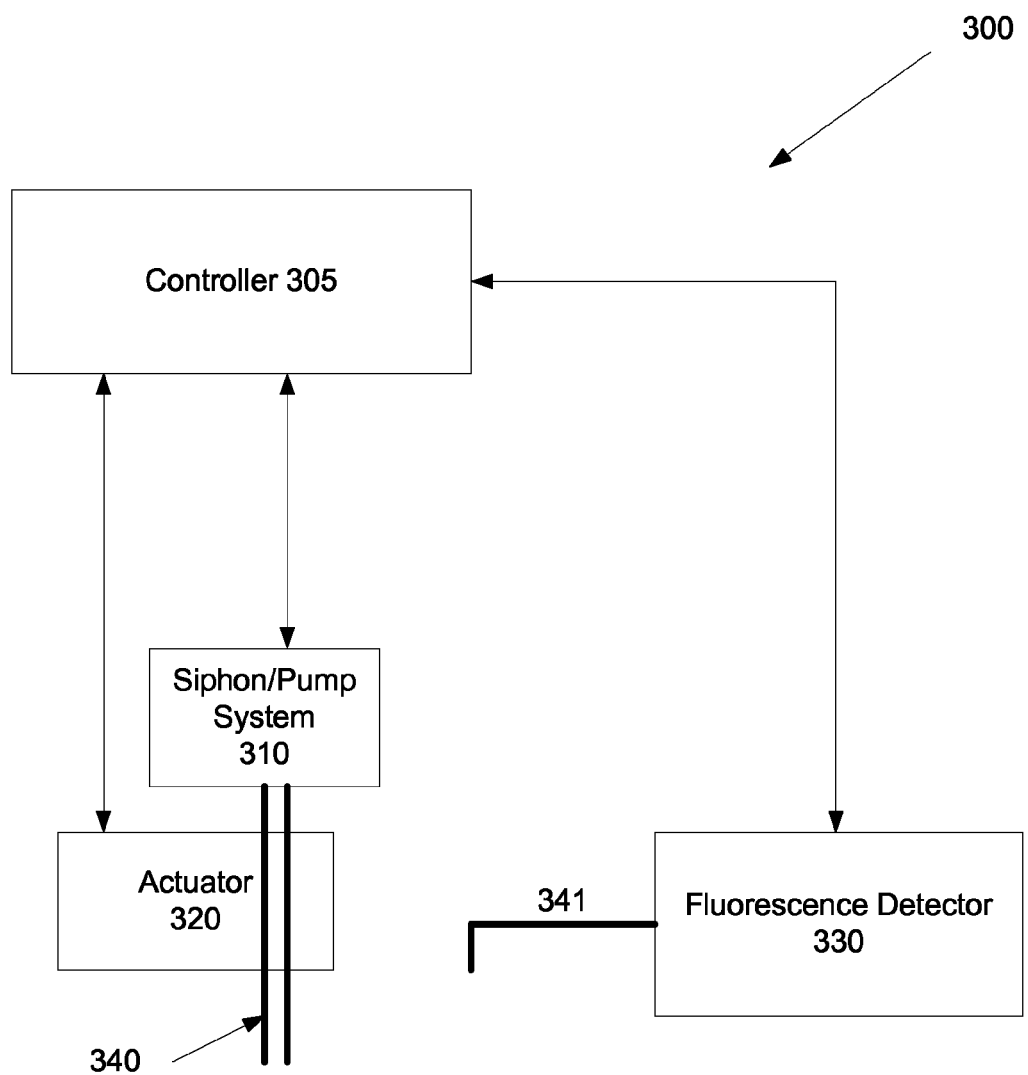
FIG. 6 is a block diagram of an apparatus adapted to perform the methods of FIG. 2 and FIG. 5.

Referring to FIGS. 3 and 6, one embodiment of the apparatus 300 will be described. The apparatus 300 uses an actuator 320 to move one of the cannulas 340 to the first well (F1). An exact amount of formulation is drawn from F1 using the siphon or pump system 310. The apparatus 300 then moves the cannula 340 so that the fluid may be expelled into F5. The apparatus 300 then uses the actuator 320 to move one of the cannulas 340, which may be the same cannula as above or a different cannula, to the third well (F3). A quantity of formulation is drawn from F3 using the siphon or pump system. 310 The apparatus then returns to F5, where the fluid is expelled into the fifth well (F5). In some embodiments, the apparatus 300 may include a mechanism to mix the formulations in F5, such as by stirring or by repeated siphoning and expelling the fluid so as to cause it to mix.

This same set of steps can then be repeated using the second well (F2), the fourth well (F4) and the sixth well (F6).

The apparatus 300 can then use the formulations in fifth well (F5) and sixth well (F6) to create a plurality of formulations which are then tested by the fluorescence detector 330. The apparatus 330 may use the actuator 320 to position a cannula 340 over the fifth well (F5) and draw an amount of the F5 formulation. The apparatus 300 may then use the actuator 320 to position a different cannula over the sixth well (F6) and draw an amount of the F6 formulation. The apparatus 300 then positions the two cannulas (either simultaneously or sequentially) over a first test well, where an amount of F5 is expelled by the first cannula and an amount of F6 is expelled by the second cannula. The apparatus 300 then positions the cannulas 340 over a second test well, where different amounts of F5 and F6 are expelled. The apparatus 300 then repeats this procedure for the desired number of test wells. The number of test wells is preferably an amount sufficient to perform a formulation study.

After the samples have been prepared in the test wells, the apparatus uses a cannula 341 (which may be one of the previously described cannulas, or a different cannula) to draw fluid from each test well and pass it to the fluorescence detector 330. The output from the fluorescence detector 330 is available as a digital output, which can then be fed to the controller 305. The controller 305 stores these outputs in a storage element, where they can be processed.

Figure 7:
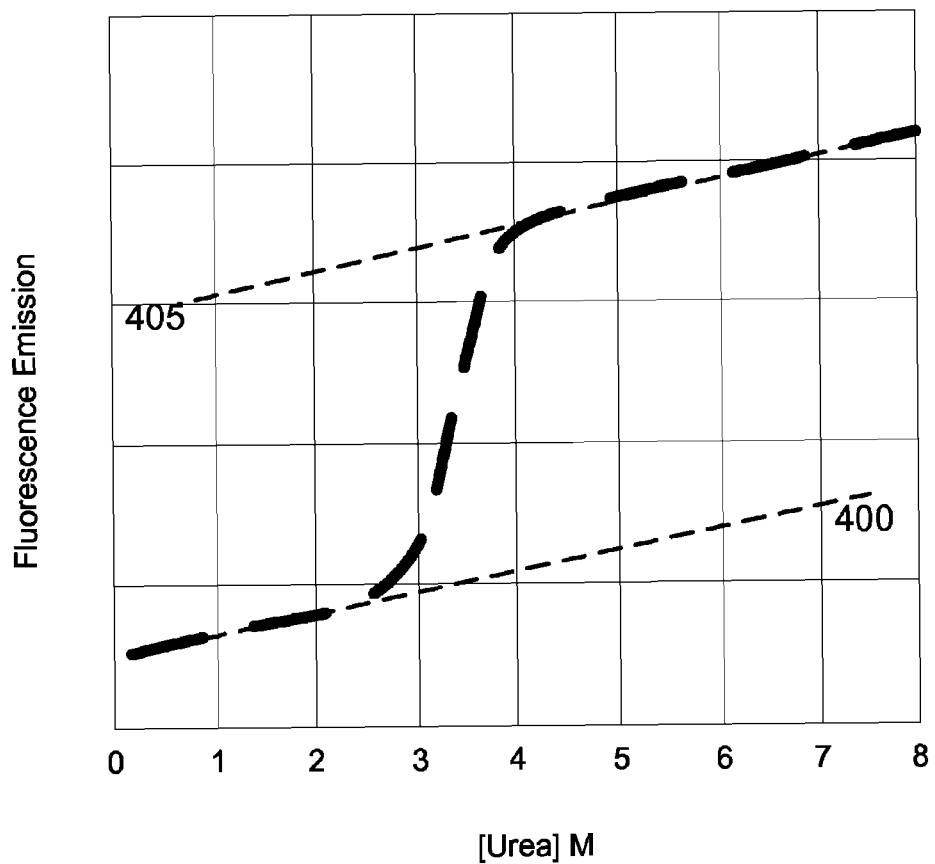
FIG. 7 shows a denaturation graph with best fit lines.

The controller 305 and its associated storage element may also include instructions to create and manipulate denaturation graphs, based on the data received from the fluorescence detector. For example, the controller 305 may select a particular wavelength which is then displayed as a graph of emission versus chemical denaturant concentration, as shown in FIG. 7. The controller 305 may then generate a best fit line 400, which corresponds to the fluorescence emission of native, or folded proteins. The controller 305 may also generate a second best fit line 405, which corresponds to the fluorescence emissions of denatured or unfolded proteins. Using these two lines 400, 405, the controller 305 may generate a second denaturation curve, which maps fraction of protein denatured as a function of chemical denaturant concentration. The value of any point on line 400 may be expressed as f(M), where M is the concentration of chemical denaturant. Similarly, the value of any point on line 405 may be expressed as g(M). Each point P on the denaturation graph can then be expressed as a fraction denatured, according to the equation, $$(P-f(M))/(g(M)-f(M)).$$

Figure 8:
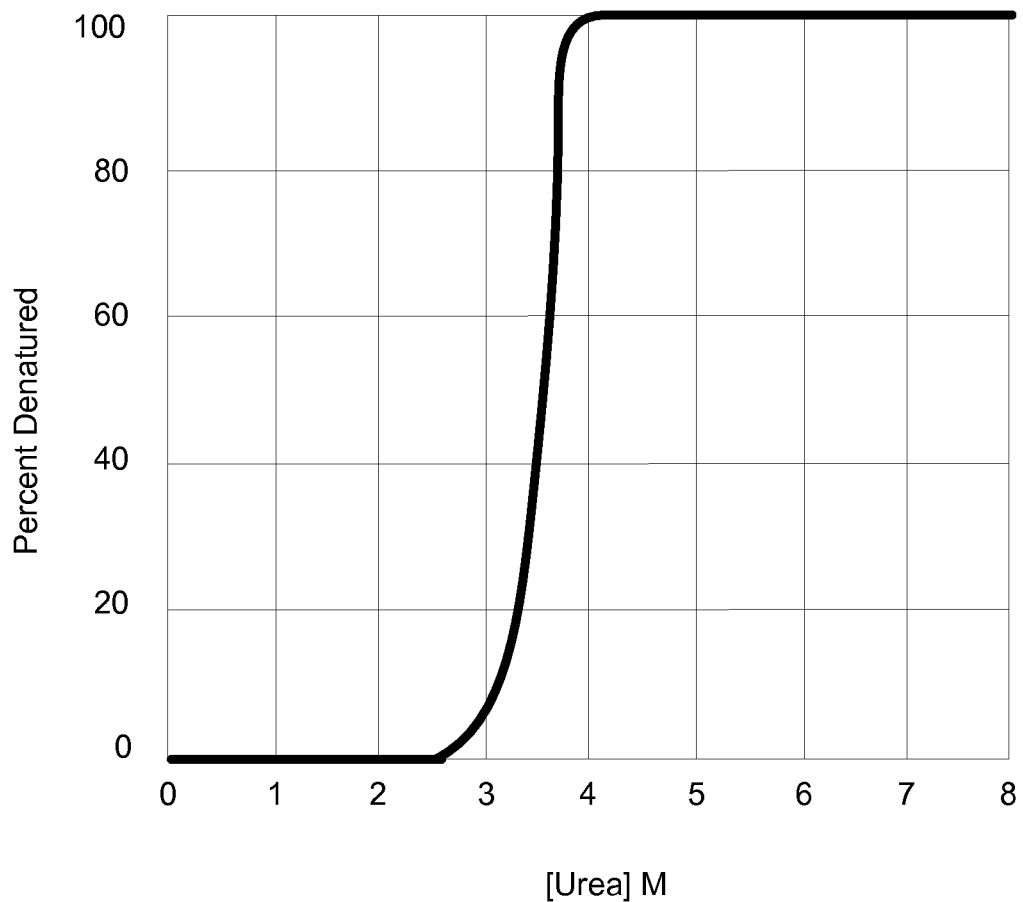
FIG. 8 shows a denaturation graph comparing percent denatured to molarity of chemical denaturant.

These points can then be used to create the denaturation graph shown in FIG. 8.

The creation of this plurality of denaturation graphs allows the analysis and study of the effect of parametric changes on the buffer solution used in conjunction with the protein at a level not previously possible.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Further, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes.

What is claimed is:

1. A method of analyzing the effect of a parameter on the stability of a protein, the method comprising:

providing a first solution with a first value of said parameter and a predetermined minimum concentration of a chemical denaturant, a second solution having said first value of said parameter and a predetermined maximum concentration of said chemical denaturant, a third solution having a second value of said parameter and said predetermined minimum concentration of said chemical denaturant, and a fourth solution having said second value of said parameter and said predetermined maximum concentration of said chemical denaturant;

combining, by an apparatus, said first solution and said third solution in various ratios to create a plurality of fifth solutions, each solution of said plurality of fifth solutions having a different value of said parameter between said first value and said second value, and having said predetermined minimum concentration of said chemical denaturant;

combining, by said apparatus, said second solution and said fourth solution in various ratios to create a plurality of sixth solutions, each solution of said plurality of sixth solutions having a different value of said parameter between said first value and said second value such that each solution of said plurality of sixth solutions corresponds to one solution of said plurality of fifth solutions, and has said predetermined maximum concentration of said chemical denaturant;

selecting, by said apparatus, a solution of said plurality of fifth solutions and a corresponding solution of said plurality of sixth solutions, such that said selected fifth and sixth solutions have the same value of said parameter;

mixing, by said apparatus, said selected fifth and corresponding selected sixth solutions in various ratios to create a plurality of seventh solutions, each solution of said plurality of seventh solutions having the same value for said parameter and a concentration of chemical denaturant between said predetermined minimum concentration and said predetermined maximum concentration;

measuring an observable property of each solution of said plurality of seventh solutions; and creating a denaturation graph based on said measured observable property of each solution of said plurality of seventh solutions and said concentration of said chemical denaturant of each solution of said plurality of seventh solutions.

2. The method of claim 1, wherein said observable property comprises fluorescence.

3. The method of claim 1, wherein said predetermined minimum concentration of chemical denaturant comprises no chemical denaturant.

4. The method of claim 1, further comprising adding a protein of interest to each of said seventh solutions prior to measuring said observable property.

5. The method of claim 1, wherein said parameter is pH.

6. The method of claim 1, wherein said parameter is salt concentration.

7. The method of claim 1, further comprising:

selecting, by said apparatus, a second solution of said plurality of fifth solutions and a corresponding second solution of said plurality of sixth solutions, such that said second selected fifth and corresponding second selected sixth solutions have the same value of said parameter;

mixing, by said apparatus, said second selected fifth solution and said corresponding second selected sixth solution in various ratios to create a plurality of eighth solutions, each solution of said plurality of eighth solutions having the same value for said parameter and a concentration of chemical denaturant between said predetermined minimum concentration and said predetermined maximum concentration;

measuring an observable property of each solution of said plurality of eighth solutions; and creating a second denaturation graph based on said measured observable property of each solution of said plurality of eighth solutions and said concentration of said chemical denaturant of each solution of said plurality of eighth solutions.

8. The method of claim 7, further comprising comparing said denaturation graph and said second denaturation graph to determine an effect of said parameter on said protein.

9. A method of analyzing the effect of a parameter on the stability of a protein, the method comprising:

providing a first formulation with a first value of said parameter and a predetermined minimum concentration of a chemical denaturant, a second formulation having said first value of said parameter and a predetermined maximum concentration of said chemical denaturant, a third formulation having a second value of said parameter and said predetermined minimum concentration of said chemical denaturant, and a fourth formulation having said second value of said parameter and said predetermined maximum concentration of said chemical denaturant;

combining, by an apparatus, said first formulation and said third formulation in a first ratio to create a fifth formulation, said fifth formulation having a value of said parameter between said first value and said second value, and having said predetermined minimum concentration of said chemical denaturant;

combining, by said apparatus, said second formulation and said fourth formulation in said first ratio to create a sixth formulation, said sixth formulation having a same value of said parameter as said fifth formulation, and having said predetermined maximum concentration of said chemical denaturant;

mixing, by said apparatus, said fifth and sixth formulations in various ratios to create a plurality of first solutions, each solution of said plurality of first solutions having the same value for said parameter and a concentration of chemical denaturant between said predetermined minimum concentration and said predetermined maximum concentration;

measuring an observable property of each solution of said plurality of first solutions; and creating a denaturation graph based on said measured observable property of each solution of said plurality of first solutions and said concentration of said chemical denaturant of each solution of said plurality of first solutions.

10. The method of claim 9, further comprising adding a protein of interest to each of said first solutions prior to measuring said observable property.

11. The method of claim 9, further comprising:

combining, by said apparatus, said first formulation and said third formulation in a second ratio to create a seventh formulation, said seventh formulation having a value of said parameter between said first value and said second value and different from said fifth formulation, and having said predetermined minimum concentration of said chemical denaturant;

combining, by said apparatus, said second formulation and said fourth formulation in said second ratio to create an eighth formulation, said eighth formulation having a same value of said parameter as said seventh formulation, and having said predetermined maximum concentration of said chemical denaturant;

mixing, by said apparatus, said seventh and eighth formulations in various ratios to create a plurality of second solutions, each solution of said plurality of second solutions having the same value for said parameter and a concentration of chemical denaturant between said predetermined minimum concentration and said predetermined maximum concentration;

measuring an observable property of each solution of said plurality of second solutions; and creating a second denaturation graph based on said measured observable property of each solution of said plurality of second solutions and said concentration of said chemical denaturant of each solution of said plurality of second solutions.

12. The method of claim 11, further comprising comparing said denaturation graph and said second denaturation graph to determine an effect of said parameter on a protein.

13. The method of claim 9, wherein said observable property comprises fluorescence.

14. The method of claim 9, wherein said predetermined minimum concentration of chemical denaturant comprises no chemical denaturant.

15. The method of claim 9, wherein said parameter is pH.

16. The method of claim 9, wherein said parameter is salt concentration.

* * * * *